United States Patent [19]

Ferenczi et al.

[11] Patent Number: 5,580,828
[45] Date of Patent: Dec. 3, 1996

[54] METHOD FOR CHEMICAL SURFACE PASSIVATION FOR IN-SITU BULK LIFETIME MEASUREMENT OF SILICON SEMICONDUCTOR MATERIAL

[75] Inventors: Gyorgy Ferenczi; Tamás Horányi, both of Budapest, Hungary

[73] Assignee: Semiconductor Physics Laboratory RT, Budapest-Ujpest, Hungary

[21] Appl. No.: 991,126

[22] Filed: Dec. 16, 1992

[51] Int. Cl.$^6$ ................................................ H01L 21/302
[52] U.S. Cl. ............................................. 437/225; 427/299
[58] Field of Search ...................................... 437/225, 228; 427/299

[56] References Cited

U.S. PATENT DOCUMENTS 3,684,592  8/1972  Chang et al. ............................ 437/225
4,973,563  11/1990  Prigge et al. ........................... 437/225

OTHER PUBLICATIONS

Article entitled "Unusually Low Surface–Recombination Velocity on Silicon and Germanium Surfaces" by Yablonovitch, D. L. Allara, C. C. Chang, T. Gmitter, T. B. Bright, pub. in Jul. 14, 1986 issue of Physical Review Letters, Vo. 57, No. 2.

Article entitled "The Passivation of Electrically Active Sites on the Surface of Crystalline Silicon by Fluorination", by B. R. Weinberger, H. W. Deckman, E. Yablonovitch, Gmitter, W. Kobasz, S. Garoff, pub. J.Vac.Sci.Technol, A3(3), May/Jun. 1985.

Article entitled "A Chemical/Microwave Technique for the Measurement of Bulk Minority Carrier Lifetime in Silicon Wafers", by Keung L. Luke and Li–Jem Cheng. J. Electrochem. Soc. Solid State Sci And Tech, Apr. 1988, pp. 957–961.

Primary Examiner—R. Bruce Breneman
Assistant Examiner—Anita Alanko
Attorney, Agent, or Firm—Walter H. Dreger, Esq.; Michael A. Kaufman, Esq.

[57] ABSTRACT

Minority carrier bulk lifetime maps are accomplished using in-situ μ-PCD measurement techniques on a non-oxidized Si specimen of either polarity. Surface passivation of the specimen is accomplished chemically, preferably using a solution of iodine in ethanol with a concentration in the range of about 0.02 mol·dm$^{-3}$ to about 0.2 mol·dm$^{-3}$. For n-type specimens, a solution of concentrated alkaline such as ammonia, sodium- and potassium-hydroxide is especially effective. For either type specimens, a solution of HF at about 40% m/m is also effective. Surface passivation according to the present invention reduces surface recombination velocities to 10 cm/second or less. The specimen to be measured is placed in a container of passivation solution such that the specimen surfaces are covered with a solution film of about 1 mm or less. The container preferably is transparent to microwave and laser optical energy, and passivation and measurement can occur simultaneously. A method and apparatus are disclosed.

19 Claims, 8 Drawing Sheets

40 μs  165 μs

280 µs  1270 µs

METHOD FOR CHEMICAL SURFACE PASSIVATION FOR IN-SITU BULK LIFETIME MEASUREMENT OF SILICON SEMICONDUCTOR MATERIAL

FIELD OF THE INVENTION

The invention relates generally to microwave or eddy current measurements of bulk lifetime carrier concentration in semiconductor materials, and more specifically to a method for chemically passivating the surface of a silicon semiconductor specimen to enhance measurement reliability.

BACKGROUND OF THE INVENTION

It is known in the art to determine semiconductor specimen purity by examining minority carrier lifetime using laser-induced microwave-detected photoconductive decay measurement systems ("μ-PCD"). One such system is disclosed in U.S. Pat. No. 4,704,576 to Tributsch, et al. (Nov. 3, 1987).

In a μ-PCD system, the specimen is exposed to a microwave field and subjected to bombardment by a pulsed laser source. The laser's photon energy induces recombination in the specimen by creating excess charge carriers, e.g., pairs of mobile electrons and holes having excess concentrations $\Delta n$ and $\Delta p$.

These carriers can affect the microwave energy reflected by the free electrons and holes in the specimen's crystal structure in a time-dependent manner. More specifically, the excess carriers increase specimen conductivity by $\Delta\sigma = q(\mu_n \Delta n + \mu_p \Delta p)$, where q is the electron charge, and $\mu_n$, $\mu_p$ are respectively electron and hole mobilities. Excess carrier concentrations $\Delta n$ and $\Delta p$ decay over time as the carriers become trapped in defects or recombine along defects within the specimen.

By detecting microwave energy reflected from the specimen, recombination decay times can be measured to determine the recombination time constant of excess carriers within the specimen. Excess conductivity ($\Delta\sigma$) measurements are indicative of defects and impurities within the specimen's crystal structure that affect the excess charge carriers.

In the simplest case, recombination is exponential with a reciprocal decay time (1/τ) proportional to the concentration of recombination centers, or impurities. Thus 1/τ (e.g., recombination lifetime) is a measure of the specimen quality.

Unless otherwise treated, the surface of a Si lattice presents many dangling bonds that can act as surface recombination centers and shorten excess carrier recombination lifetime. Because μ-PCD and eddy current techniques seek to measure bulk recombination and not the more rapidly occurring surface recombination, measurements typically have been made on a Si surface that is treated by thermal oxidation or chemical passivation. A significant deficiency of μ-PCD and eddy current measurements on non-oxidized wafers is that bulk lifetime cannot even be estimated if bulk lifetime is too large.

It would be advantageous to make stable μ-PCD or eddy current measurements on non-oxidized specimens for several reasons. Such measurements would avoid furnace contamination of the specimen associated with thermal oxide growing, and would avoid the problems associated with producing high quality stable, oxidized Si surfaces. Further, it is important to characterize "as-grown" (e.g., non-oxidized) Si wafers without high temperature alteration of the original distribution of any contaminants and/or the nature of crystal defects.

One known technique for chemical passivation of Si has been to initially provide an HF acid etch and then use various acid solutions. E. Yablonovitch, et al. report in *Phys. Rev. Letters* 57 (1986) 249 that this alternative to thermal oxidation produces an ideal (electronically inactive) surface with very low surface recombination velocity (S). In fact, this reference reports surface recombination velocities as low as about 0.25 cm/sec, and states that these values were apparently the lowest value ever reported for any semiconductor. Unfortunately, Yablonovitch, et al.'s passivation technique is limited to measuring carrier-density decay on individual points in the chemically passivated wafer.

Notwithstanding the early success of E. Yablonovitch, et al., what is needed is a method of chemically passivating a Si specimen that significantly decreases surface recombination velocity (S). What is needed is a passivation method that permits mapping bulk lifetime for an entire area, rather than mapping only individual lattice points. Preferably such passivation technique should approximate the perfection of an Si-SiO$_2$ interface, and permit reliable in-situ bulk lifetime measurement on as-grown Si specimens. The present invention discloses a method and apparatus for accomplishing such chemical passivation.

SUMMARY OF THE INVENTION

The present invention permits simultaneous chemical surface passivation of a silicon specimen and in-situ minority bulk lifetime mapping over the entire specimen.

The specimen is positioned in a suitable container and covered with sufficient passivation solution to form a film on the specimen.

The present invention provides an iodine containing passivation solution that lowers surface recombination velocities for n-type and p-type materials to 10 cm/sec or less. Alternatively, for n-type material, passivation is also achieved using a concentrated alkaline solution. Finally, for either type silicon, passivation may also be obtained with an acidic solution containing fluoride ions.

Other features and advantages of the invention will appear from the following description in which the preferred embodiments have been set forth in detail in conjunction with the accompanying drawings.

DETAILED DESCRIPTION OF THE PREFERRED EMBODIMENTS

Figure 1:
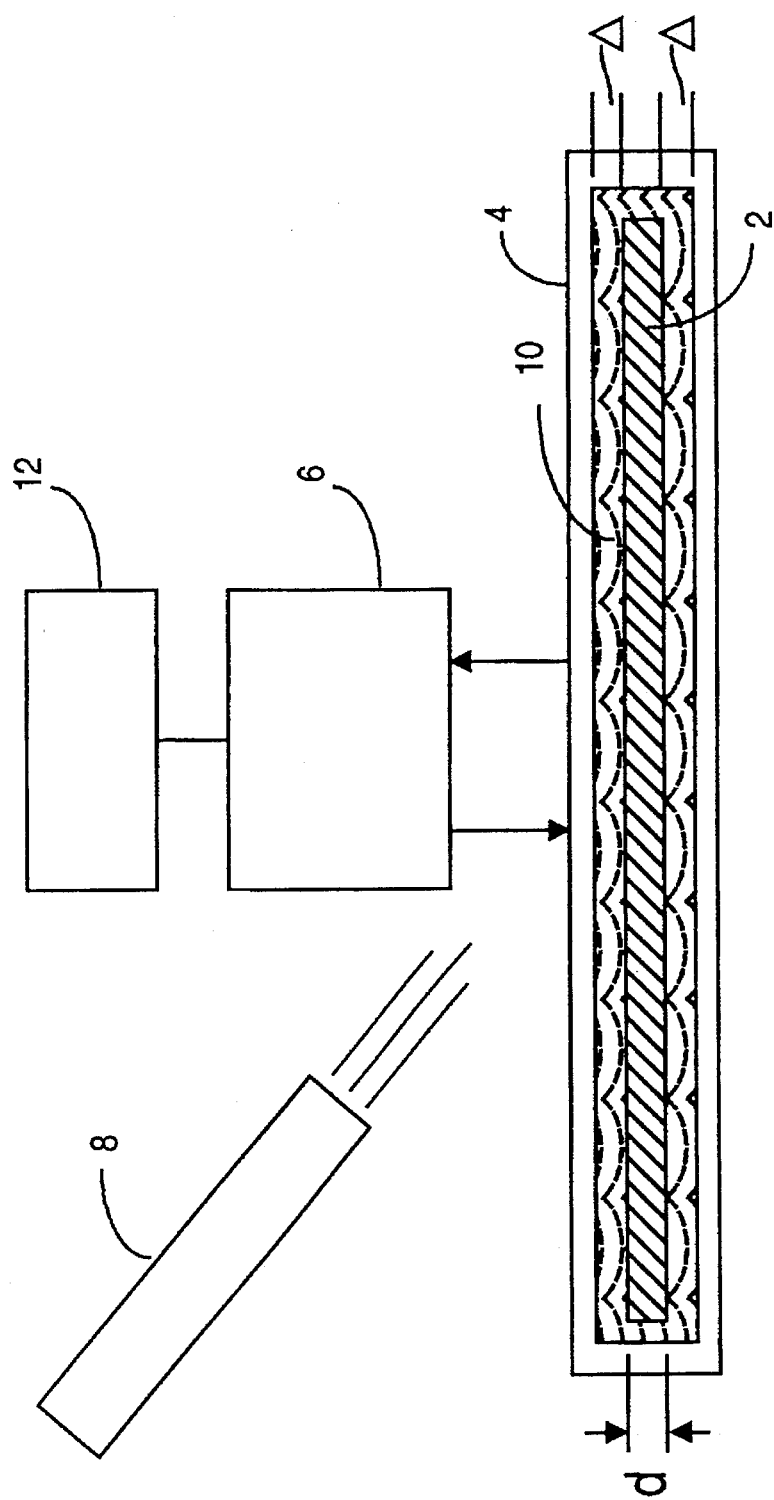
FIG. 1 depicts generally a μ-PCD type system with which the present invention may be practiced.

FIG. 1 depicts a µ-PCD system with which the present invention may be practiced, although an eddy current system could also be used. A semiconductor specimen 2 having thickness d is positioned within a container 4 and subjected to microwave energy from microwave source and microwave reflection measuring unit 6 and to pulsed optical energy from laser source 8. Preferably container 4 is fabricated from a material that is transparent both to microwave and optical energy, e.g., a plastic, or a plastic container with glass windows. Container 4 holds a passivation solution 10 according to the present invention, which solution covers the upper and lower surfaces of specimen 2 to a desired film thickness Δ that preferably is less than about 1 mm, and may in fact be less than about 0.1 mm.

Laser source 8 is pulsed, and photons therefrom create minority carriers within specimen 2. More specifically, laser photoexcitation causes the simultaneous injection of electron-hole pairs in the specimen, and recombination occurs at each deep level present therein.

Microwave energy from unit 6 reflects from free electrons and holes in specimen 2, which reflection is affected by minority carrier recombination lifetimes. A detector within microwave reflection measuring unit 6 detects these reflections, and the detector output signals are processed by processor 12 to characterize electron and hole recombination within the specimen. Processor 12 typically includes a digital computer and appropriate video monitor and/or plotter output that display operator selected information relating to impurities and their location within the specimen. Such information can include high resolution lifetime maps of a specimen under test, passivated according to the present invention.

In the embodiment of FIG. 1, unit 6 provides a 10.3 GHz microwave signal, and laser source 8 is a 904 nm GaAs device whose output was concentrated on a spot smaller than about 1 mm² at the upper surface of specimen 2, with injected carrier density between about $10^{15}/cm^3$ and $10^{17}/cm^3$. Processor 12 preferably includes a computer-controlled WT-85 lifetime scanner, manufactured by Semilab Corporation of Budapest, Hungary.

In a manner known to those skilled in the art, with the onset of each laser optical pulse, the output from microwave reflection measuring unit 6 increases sharply in proportion to the change in conductivity (Δσ) of the specimen. The detector output waveform from microwave reflection measuring unit 6 then decays toward a baseline level with a time constant proportional to the minority carrier recombination lifetime.

Because details of µ-PCD and eddy-current measuring systems are known to those skilled in the relevant art, further details of such systems and measurements are not presented.

µ-PCD can be an effective tool for high resolution lifetime mapping on a whole semiconductor wafer specimen. The technique can provide valuable information about lateral distribution of contaminants such as crystal growth defects, metal contaminants, etc. on "as-grown" (non-oxidized) wafers). However µ-PCD is not suitable for estimating absolute impurity concentration levels because the measured lifetime of a non-oxidized specimen is not determined primarily by bulk recombination, but rather by surface recombination and carrier diffusion.

As noted, while thermal oxidation of a Si specimen allows bulk recombination to predominate lifetime measurements, the thermal process of growing the oxide undesirably can alter characteristics of the specimen under test.

According to the present invention, lattice termination is achieved by chemically passivating the specimen surface. Such passivation according to the present invention approximates the perfection of an $Si-SiO_2$ interface, and permits in-situ µ-PCD bulk lifetime measurement on as-grown Si wafers.

The theoretical relationship between the voltage transient from the microwave reflection measuring unit 6 and the parameters of specimen 2 is well known. Accordingly, the effective time constant $\tau_{eff}$ calculated from the exponential shape of the conductivity decay curve may be written as:

$$\frac{1}{\tau_{eff}} = \frac{1}{\tau_b} + \frac{1}{\tau_s} \qquad (1)$$

where $\tau_b$ is bulk minority carrier lifetime, and $\tau_s$ relates decay time to surface recombination.

It is known that $\tau_s$ may be obtained by solving the time-dependent equation for excess carrier density. So doing yields a transcendental equation for $\tau_s$ as follows:

$$\alpha \cdot \tan\left(\frac{\alpha \cdot d}{2}\right) = \frac{S}{D_n}, \text{ where } \frac{1}{\tau_s} = D_n \cdot \alpha^2 \qquad (2)$$

and where $D_n$ is the minority carrier diffusion constant, S is the surface recombination velocity, and d is the thickness of the semiconductor specimen under test.

Consider the two limiting cases, where surface recombination velocity S is large and where S is small. For small surface recombination velocity, $(S<<D_n)$, $\tau_s=2S/d$, and for large surface recombination velocity $(S>>D_n)$, $\tau_s=D_n\pi^2/d^2$. Rather than use one of the above expressions, applicants chose to approximate $\tau_s$ as follows:

$$\tau_s = \frac{d^2}{\pi^2 \cdot D_n} + \frac{d}{2 \cdot S} \qquad (3)$$

Figure 2:
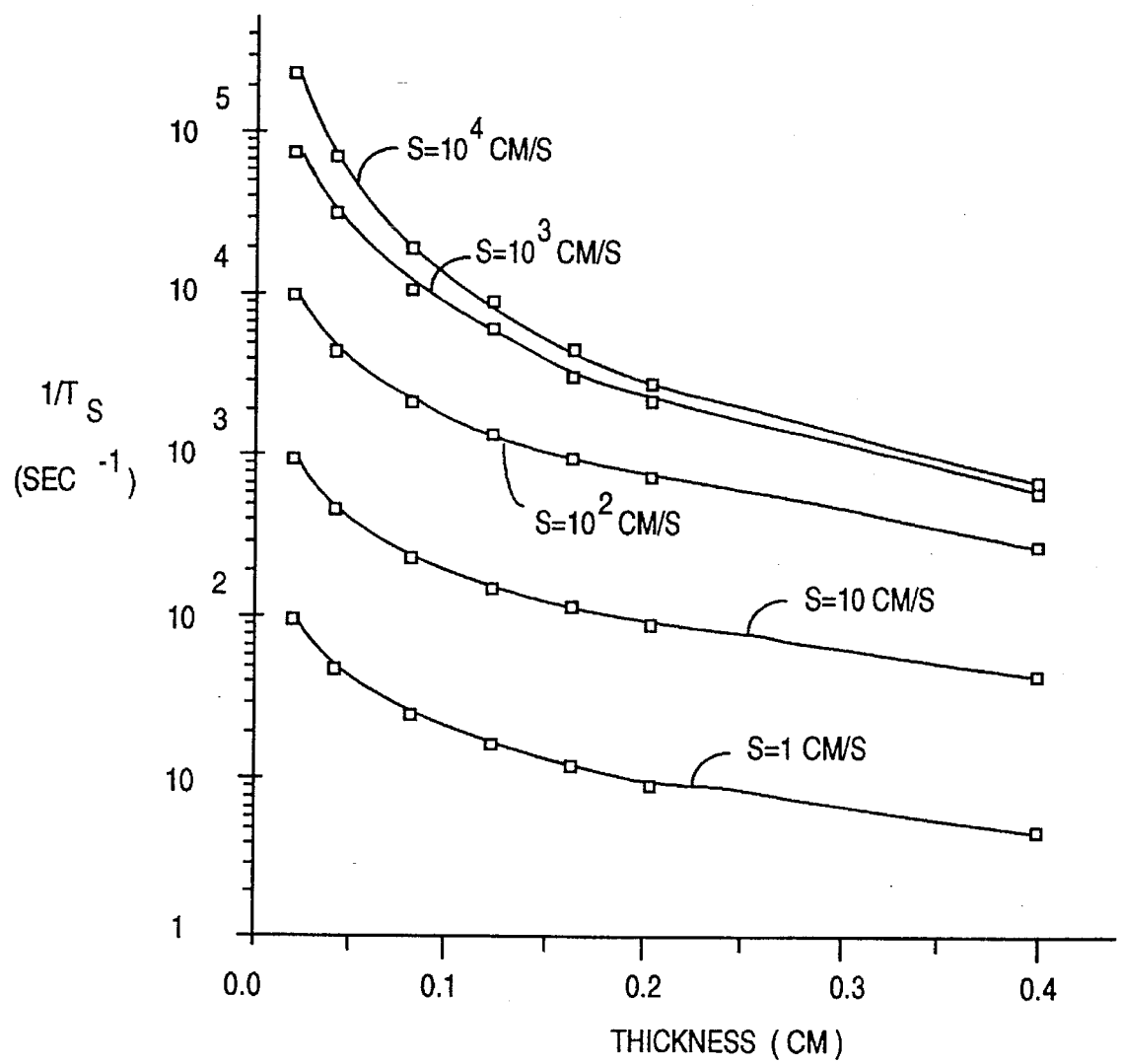
FIG. 2 depicts, for different surface recombination velocities, the close agreement between theoretical $\tau_s$ and $\tau_s$ calculated from applicants' approximating equation (3)

For different surface recombination velocities, FIG. 2 depicts the close agreement between $\tau_s$ calculated from theoretical equation (2), and $\tau_s$ calculated from applicants' equation (3). In the following discussion, applicants' equation (3) shall be relied upon.

With reference to FIG. 2, applicants initially prepared various passivating solutions 10 using analytical grade reagents. Because the effectiveness of surface passivation is highly dependent upon pre-lifetime measurement surface treatment, applicants initially etched the non-polished surfaces of specimen 2. An etching solution containing HF and $HNO_3$ was applied to prepare the surfaces of the non-polished Si wafer specimens for subsequent µ-PCD measurements.

Various solutions containing HF and $HNO_3$ proved to be suitable for pre-lifetime measurement surface treatment, including standard $HF:HNO_3:CH_3COOH$ (22:47:31). Applicants believe that optimal preparation of the semiconductor specimen surface may be dependent upon the surface quality, e.g., polished, non-polished, hydrophobic, hydrophilous, etc. Thus in practice, front and back surfaces of non-polished wafers were etched, and no etching was performed on polished wafers.

Figure 3:
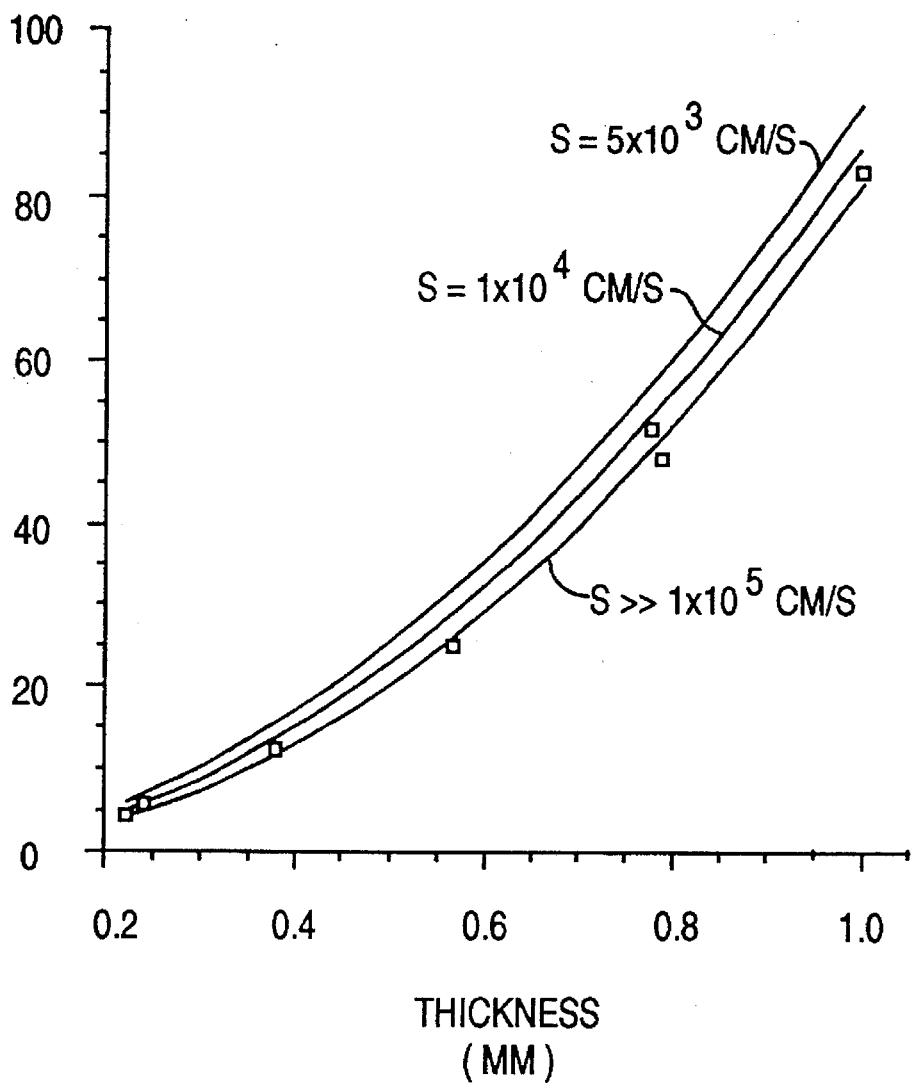
FIG. 3 depicts dependence of surface recombination related decay time ($\tau_s$) and thickness for an n-type Si specimen.

That the average effective recombination lifetime values for such wafers is determined principally by the rate of the diffusion process of minority carriers is borne out by FIG. 3. FIG. 3 depicts the average effective recombination lifetime for various non-oxidized polished and non-polished n-type Si wafers having different thicknesses d, with high expected bulk lifetimes. The data plotted in FIG. 3 correspond to the effective lifetime values calculated using equations (1) and (3) at different surface recombination velocities (S), assuming that $1/\tau_b$ is negligible, such that consequently $\tau_{eff} \approx \tau_s$.

With further reference to FIG. 3, as all measured data points were below the curve calculated at $S=10^4$ cm/sec, applicants conclude that the surface recombination velocity of the wafers initially tested probably exceeded this velocity.

Figure 4A:
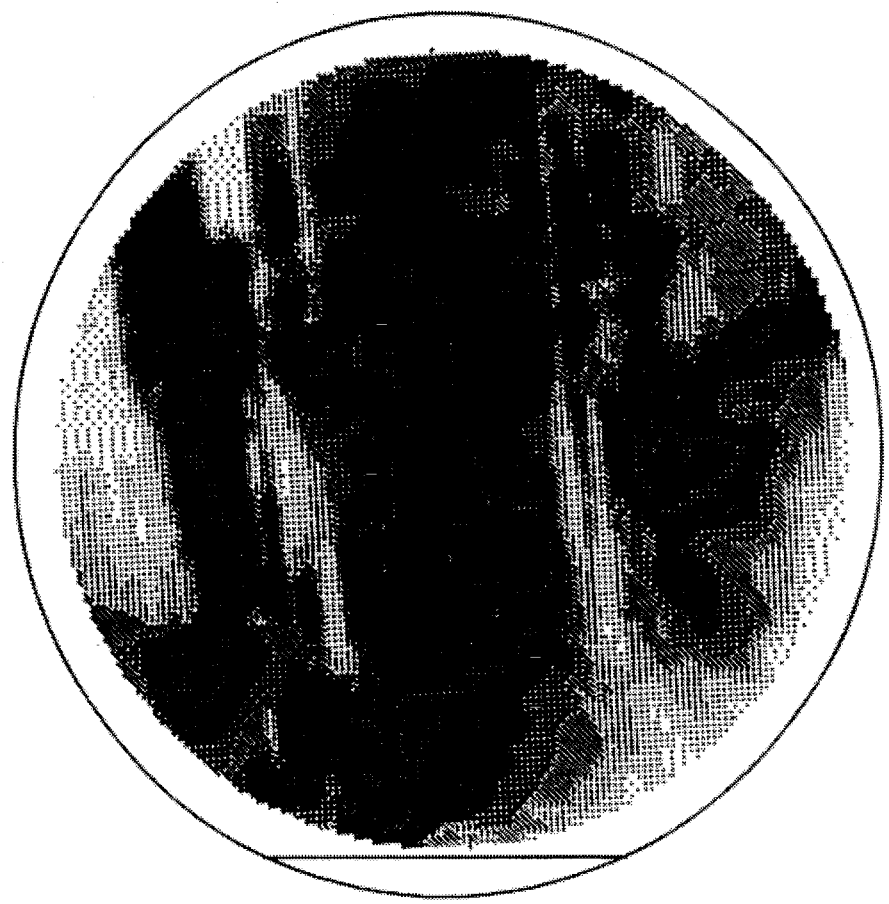
FIG. 4A is a high resolution lifetime map of p-type <100> Si with an oxidized surface, average effective lifetime $\tau_{eff} \approx 102$ μs.
Figure 4A:
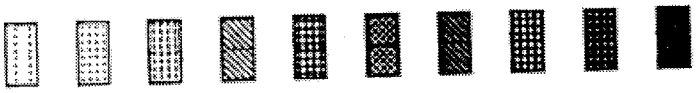
Figure 4B:
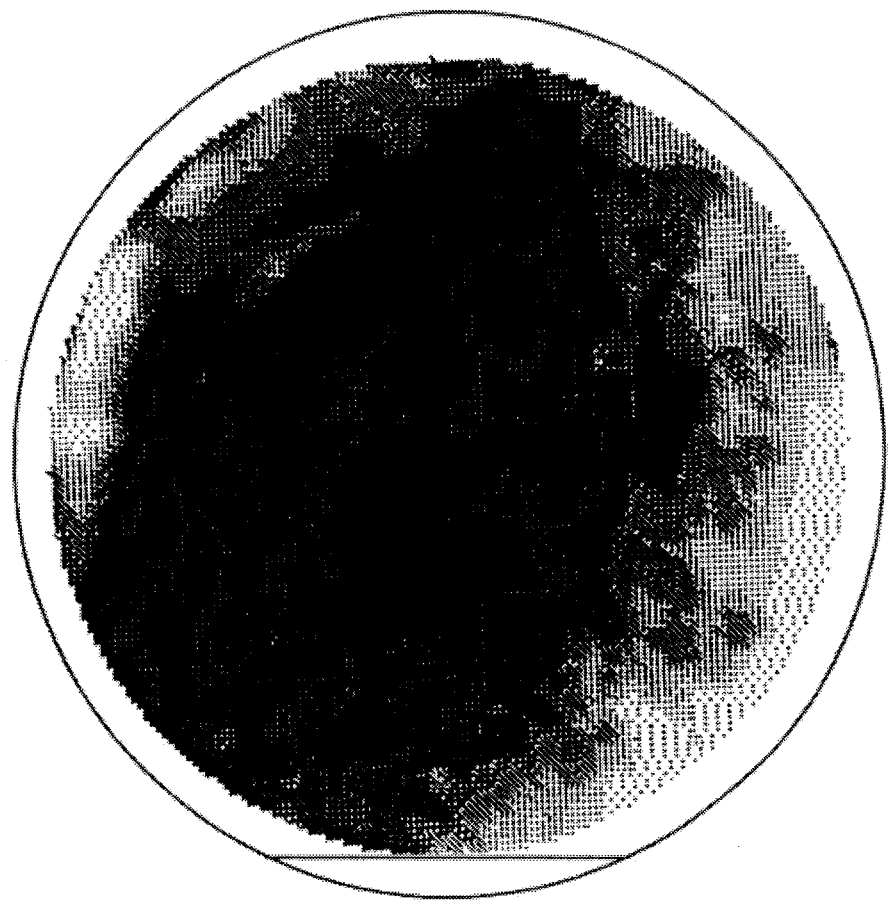
FIG. 4B is a high resolution lifetime map for the same p-type specimen initially used in FIG. 4A, with the oxide layer removed, average effective lifetime $\tau_{eff} \approx 17.4$ μs.
Figure 4B:
Figure 4C:
FIG. 4C is a high resolution lifetime map for the same p-type specimen used in FIG. 4A and 4B, where the non-oxidized wafer is chemically passivated according to the present invention, average effective lifetime of $\tau_{eff} \approx 115$ µs.
Figure 4C:

FIGS. 4A–4C are high resolution lifetime maps for the same p-type <100> specimen, under various surface conditions. Interestingly, the measured lifetime map of FIG. 4B (non-oxidized surface) mirrors the distribution of bulk parameters, as is appreciated by comparison with the lifetime map of FIG. 4A (oxidized surface). These data reflect the inapplicability of μ-PCD measurement to the determination of bulk minority carrier lifetime of non-oxidized wafers, at least according to the prior art.

FIGS. 4A and 4C demonstrate the effectiveness of surface passivation according to the present invention. The figures strongly suggest that the surface recombination velocity of the chemically passivated surface according to the present invention (FIG. 4C) is basically the same as the surface recombination velocity of the thermally oxidized surface (FIG. 4A).

Applicants found three groups of passivation solutions to be applicable for the surface passivation of Si. These groups were (1) various fluoride ion containing acidic solutions, (2) concentrated alkaline solutions including ammonia, sodium-hydroxide and potassium-hydroxide solutions, and (3) and solutions containing iodine, especially ethanol and iodine, or hydrodic acid and iodine.

Table 1 below depicts effective lifetime values measured in various of these passivating solutions for float-zone produced p-type and n-type specimens, having thickness d =2 mm. Similar data would be expected for CZ-produced specimens as well.

TABLE 1

| | EFFECTIVE LIFETIME (μs) | |
|---|---|---|
| PASSIVATION SOLUTION | n-type <111> 9 Ω-cm | p-type <100> 18 Ω-cm |
| none | 231 | 79 |
| HF (40% m/m) | 474 | 500 |
| NaOH (4 mol · dm$^{-3}$) | 871 | 217 |
| Iodine in ethanol (0.08 mol · dm$^{-3}$) | 725 | 631 |

Table 1 reflects that for n-type material, the highest effective lifetime (e.g., that corresponding to the lowest surface recombination velocity S) was obtained in an NaOH alkaline solution. However the same solution showed poor effectiveness in passivating p-type Si.

Applicants noted that independent of specimen type, using alkaline solution passivation, Si dissolution was accompanied by hydrogen gas evolution. P-type Si has a higher dissolution rate and this gas evolution produced a discolored, rough surfaces for p-type specimens. By contrast, at low alkaline solution concentrations wherein gas evolution was absent, no passivation effect was observed during μ-PCD measurement.

Table 1 also reflects that passivation with an iodine solution provided a higher effective lifetime that passivation with an acidic fluoride solution, regardless of specimen type.

Based upon the data of Table 1, applicants experimentally determined that an iodine ($I_2$) concentration from about 0.02 mol·dm$^{-3}$ to 0.2 mol·dm$^{-3}$ was especially suitable for surface passivation of Si of either polarity. At lower iodine concentrations, the measured lifetime value decreased considerably, and at higher concentration, a slight decrease in effective lifetime value was detected during μ-PCD measurement. Possibly the latter effect is attributable to the slow oxidation of Si in the iodine solution.

From equations (1) and (3) it is clear that at sufficiently low surface recombination velocity (S), the measured effective lifetime is a good approximation of the bulk lifetime value.

Figure 5:
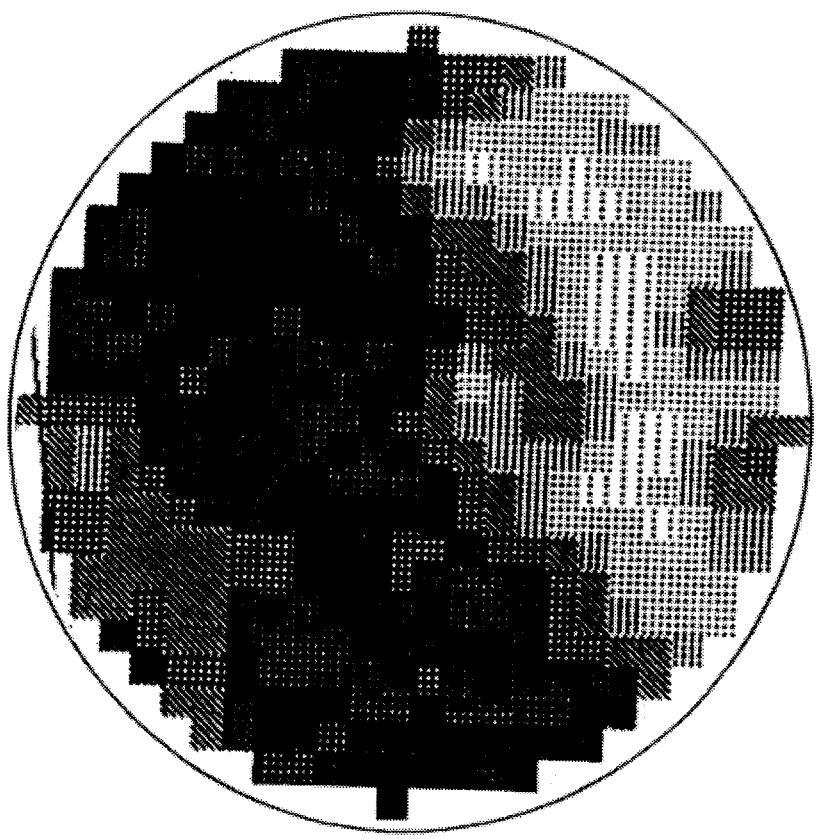
FIG. 5 is a lifetime map made from a 200 µm thick n-type <111> Si, 25 Ω-cm, float-zone produced specimen, using chemical surface passivation according to the present invention, average effective lifetime $\tau_{eff} \approx 763$ µs.
Figure 5:

FIG. 5 is a lifetime map of a relatively thin Si wafer (d=200 μm). This lifetime map measurement is used to estimate an upper limit for the surface recombination velocity of the specimen under test.

Assuming that the upper value of effective lifetime is limited by the surface recombination process (e.g., $\tau_s > \tau_{eff}$), an upper limit for the surface recombination velocity is:

$$S < \frac{d}{2 \cdot (\tau_{eff} - d^2/\pi^2 \cdot D_n)} \quad (4)$$

The above limit corresponds to a relatively low value S<10 cm/sec for the case depicted in FIG. 5. This surface recombination velocity value is sufficiently low for bulk lifetime measurements on standard size wafers (d>0.5 mm). This conclusion follows because deviation of the effective lifetime value from the bulk lifetime is less than about 30%, even if the expected bulk lifetime is $10^3$ seconds.

Figure 6:
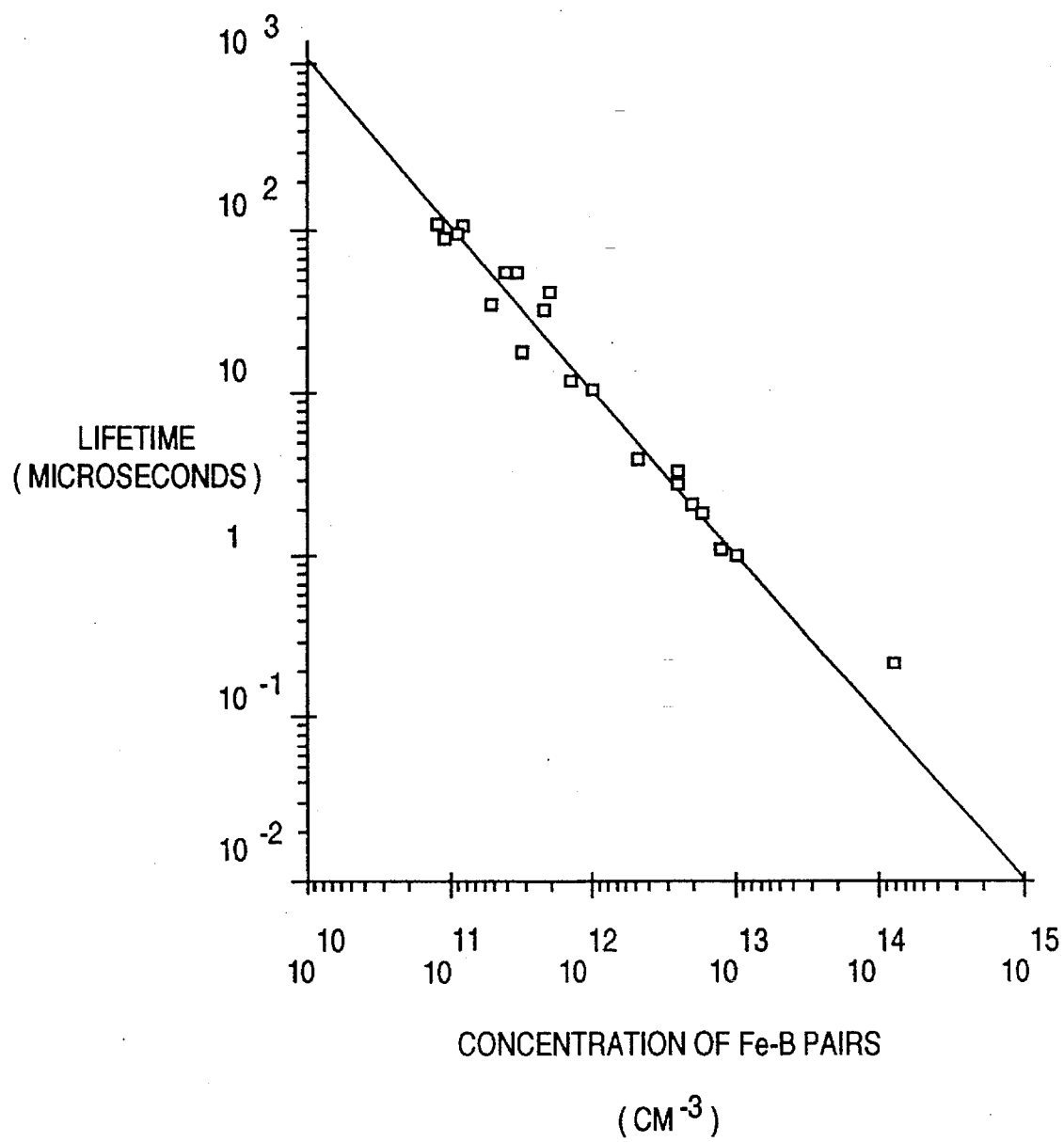
FIG. 6 shows correlation between iron concentration and minority carrier lifetime in p-type silicon.

FIG. 6 confirms the above finding and demonstrates excellent correlation between Fe—B pair recombination centers and the measured effective lifetime values. It is known in the art that the presence of Fe in Si, even in low concentration, substantially reduces lifetime. For a p-type boron-doped specimen, iron is present in the form of an Fe—B pair. In such specimens, the concentration of the Fe—B pair recombination centers may be accurately determined using deep level transient spectroscopy ("DLTS") techniques. DLTS techniques are known to those skilled in the relevant art, and details are therefore not presented here.

The linearity of the correlation curve shown in FIG. 6 is a good indication of the reliability of bulk lifetime measurement, using chemical surface passivation according to the present invention. This conclusion follows because recombination probability, or the reciprocal lifetime $1/\tau_b$, is proportional to the concentration of the recombination centers. As noted, FIGS. 4A and 4C further bear out the integrity of surface passivation according to the present invention.

Various modifications of the present invention may occur to those skilled in the art without departing from the true spirit and scope of the invention, as defined by the appended claims.

What is claimed is:

1. A method for surface passivation of a semiconductor specimen that is subjected to in-situ bulk lifetime measurement during said surface passivation, the method comprising the following steps:

(a) providing a passivation solution including iodine, said passivation solution selected to reduce surface recombination velocity of the specimen below about 906 cm/second;

(b) surrounding the specimen with said passivation solution such that both surfaces of the specimen are covered with at least a film of said solution;

wherein surface recombination velocity of the specimen is reduced below about 906 cm/sec and wherein passivation is achieved without heating said specimen.

2. The method of claim 1, wherein at step (a), said solution includes ethanol.

3. The method of claim 1, wherein at step (a), said solution has an iodine ($I_2$) concentration ranging from about 0.02 mol·dm$^{-3}$ to about 0.2 mol·dm$^{-3}$.

4. The method of claim 1, wherein at step (b), said film has a thickness less than about 1 mm.

5. The method of claim 1, wherein at step (a), said solution reduces surface recombination velocity of the specimen below about 10 cm/second.

6. A method for surface passivation of a semiconductor specimen that is subjected to in-situ bulk lifetime measurement during said surface passivation, the method comprising the following steps:

(a) providing a passivation solution including concentrated alkaline, said passivation solution selected to reduce surface recombination velocity of the specimen below about 906 cm/second;

(b) surrounding the specimen with said passivation solution such that the upper and lower surfaces of the specimen are covered with at least a film of said solution;

wherein surface recombination velocity of the specimen is reduced below about 906 cm/sec., and wherein passivation is achieved without heating said specimen.

7. The method of claim 6, wherein at step (a), said solution includes at least one constituent selected from the group consisting of ammonia, sodium-hydroxide, and potassium-hydroxide.

8. The method of claim 6, wherein at step (a), said solution has an alkaline concentration of about 4 mol·dm$^{-3}$.

9. The method of claim 6, wherein at step (b), said film has a thickness less than about 1 mm.

10. A method of producing in-situ bulk lifetime measurements over a continuous area of a non-oxidized silicon semiconductor specimen, the method comprising the following steps:

(a) providing a passivation solution containing iodine, said passivation solution selected to reduce surface recombination velocity of the specimen below about 906 cm/sec.;

(b) surrounding the specimen with said passivation solution such that both surfaces of the specimen are covered with at least a film of said solution, said film having a thickness less than about 1 mm;

(c) subjecting the specimen to energy from a microwave source and from a pulsed optical source;

said optical energy creating within at least a region of said specimen carrier pairs that begin to recombine upon cessation of each optical energy pulse;

(d) detecting microwave energy reflected by freed carriers in said specimen;

wherein surface recombination velocity of the specimen is reduced below about 906 cm/sec. and detected reflected microwave energy characterizes minority carrier recombination lifetime within said specimen and provides information as to defects therein.

11. The method of claim 10, wherein at step (a) said solution includes iodine and ethanol.

12. The method of claim 10, wherein at step (a) said solution has an iodine ($I_2$) concentration ranging from about 0.02 mol·dm$^{-3}$ to about 0.2 mol·dm$^{-3}$.

13. The method of claim 10, wherein at step (a) said film is selected to reduce surface recombination velocity of the specimen below about 100 cm/sec.

14. The method of claim 10, wherein at step (b) said solution is selected to reduce surface recombination velocity of the specimen below about 10 cm/second.

15. The method of claim 10, wherein at step (a), said solution includes NaOH at a concentration of about 4 mol·dm$^{-3}$.

16. The method of claim 10, wherein at step (a), said solution is HF at a concentration of about 40% m/m.

17. The method of claim 1, wherein at step (a), said solution reduces surface recombination velocity of the specimen below about 100 cm/second.

18. The method of claim 6, wherein at step (a), said solution reduces surface recombination velocity of the specimen below about 100 cm/second.

19. The method of claim 6, wherein at step (a), said solution reduces surface recombination velocity of the specimen below about 10 cm/second.

* * * * *